United States Patent
Sadri

(10) Patent No.: US 9,557,293 B2
(45) Date of Patent: Jan. 31, 2017

(54) HIGH-THROUGHPUT MULTI-LASER WAVE MIXING DETECTION METHODS AND APPARATUS

(71) Applicant: Behrokh Bagherifar Sadri, San Diego, CA (US)

(72) Inventor: Behrokh Bagherifar Sadri, San Diego, CA (US)

( * ) Notice: Subject to any disclaimer, the term of this patent is extended or adjusted under 35 U.S.C. 154(b) by 0 days.

(21) Appl. No.: 14/571,185

(22) Filed: Dec. 15, 2014

(65) Prior Publication Data

US 2015/0168347 A1    Jun. 18, 2015

Related U.S. Application Data

(63) Continuation of application No. 13/586,876, filed on Aug. 16, 2012, now abandoned.

(51) Int. Cl.
G01N 1/10          (2006.01)
G01N 27/447      (2006.01)

(52) U.S. Cl.
CPC .. *G01N 27/44791* (2013.01); *G01N 27/44721* (2013.01)

(58) Field of Classification Search
CPC ............ G01N 27/447; H01S 3/00; G02B 5/04
See application file for complete search history.

(56) References Cited

U.S. PATENT DOCUMENTS

2012/0219029 A1*  8/2012  Scott ......................... G01J 3/10
                                                                     372/38.02

OTHER PUBLICATIONS

"Protein Analysis at the Single Cell Level by Nonlinear Laser Wave-Mixing Spectroscopy for High Throughput Capillary Electrophoresis Applications", North Carolina State University, Raleigh, North Carolina, 2008 by Behrokh Bagherifar Sadri.*

* cited by examiner

*Primary Examiner* — Tarifur Chowdhury
*Assistant Examiner* — Jamil Ahmed
(74) *Attorney, Agent, or Firm* — John A. Barrett

(57) ABSTRACT

This invention relates to methods and apparatus of a combination of multi-laser wave mixing technology with diagnostic flow system with embodiments describing capillary electrophoresis. The unique combination of these technologies along with minute detection levels not yet been seen in the field.

2 Claims, 2 Drawing Sheets

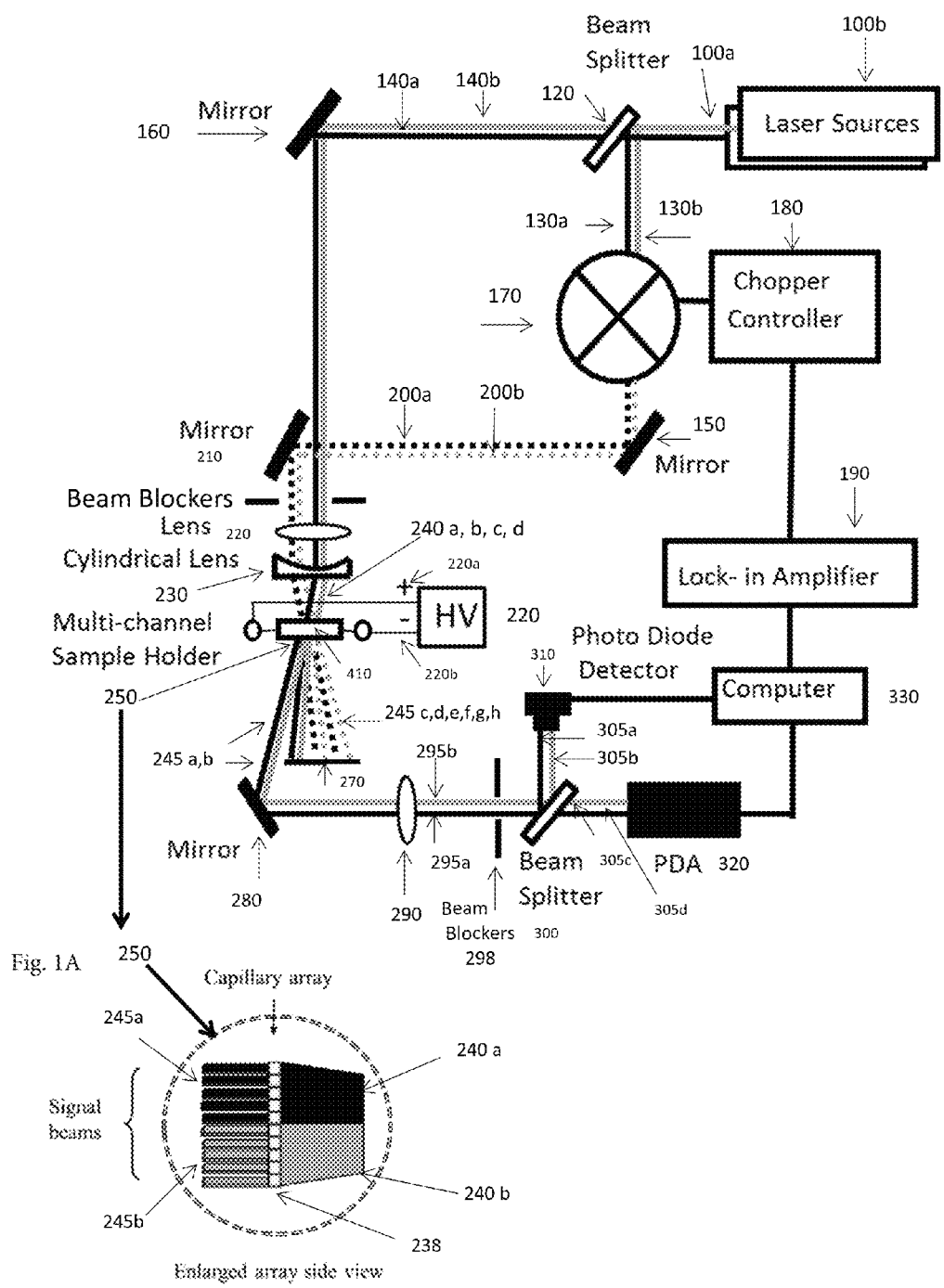

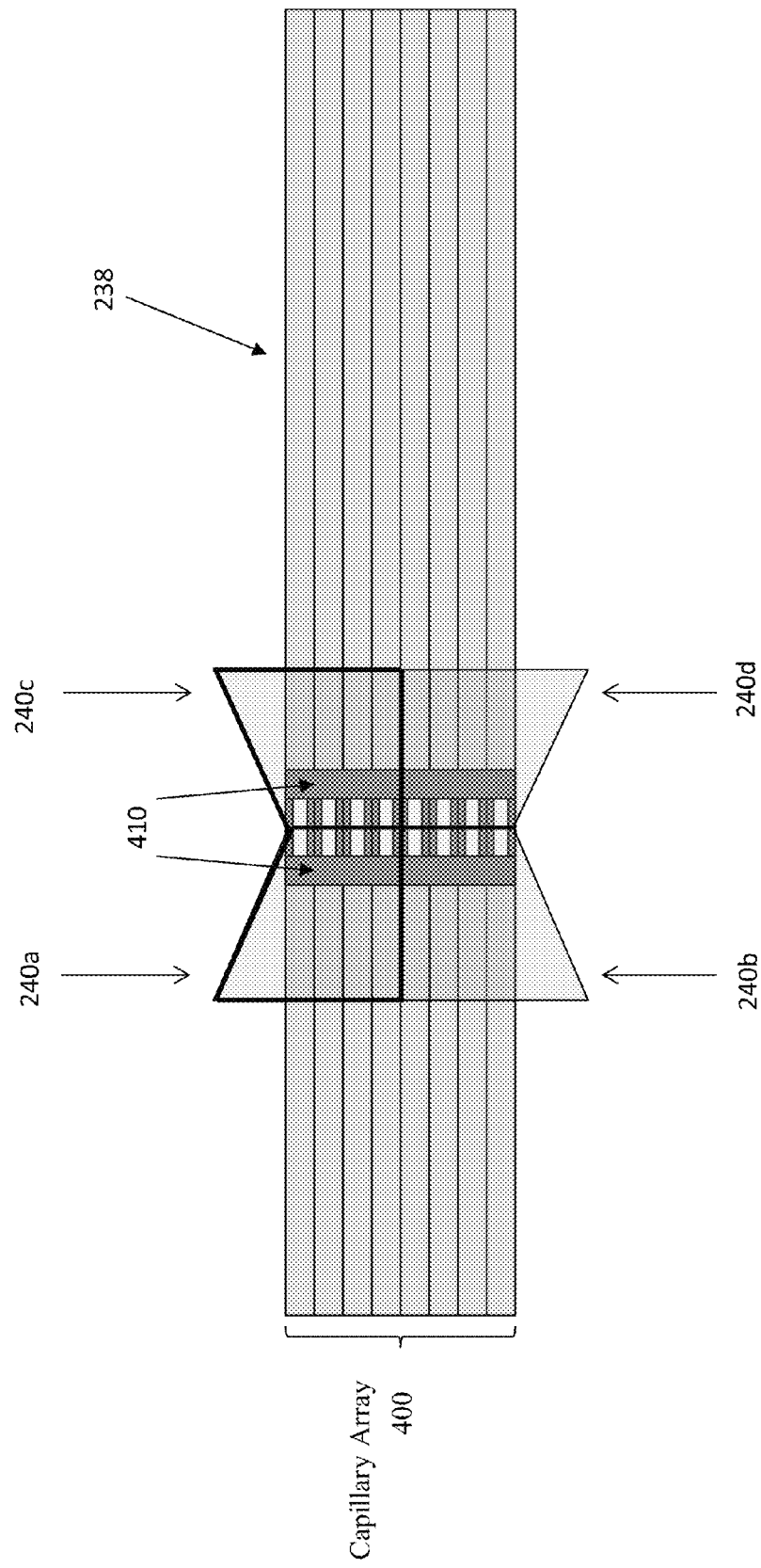

HIGH-THROUGHPUT MULTI-LASER WAVE MIXING DETECTION METHODS AND APPARATUS

This is a continuation application claiming priority under 35 U.S.C. §120 to U.S. non-provisional application Ser. No. 13/586,876 filed Aug. 16, 2012 (EST) which is hereby incorporated by reference in its entirety.

This invention relates to methods and apparatus of a combination of laser wave mixing technology with capillary electrophoresis diagnostic flow technologies. The combination of these technologies along with minute detection levels not yet been seen in the field.

BACKGROUND

Laser wave mixing has been described in many patents, journals and articles. Having greatest relation to embodiments of the invention described herein are Tong has described degenerate four wave mixing and apparatus therein in U.S. Pat. Nos. 5,600,444 and 6,141,094 and Patent Application 2006263777. These describe apparati and methods that in their capacities are capable of analyzing small quantities of analytes down to a detection level of attomoles. They utilize different complements of analysis systems including HPLC and HCPE and a gas phase atomizer type spectroscopy. Furthermore, the dissertation "Protein Analysis at the Single Cell Level by Nonlinear Laser Wave-Mixing Spectroscopy for High Throughput Capillary Electrophoresis Applications" from Sadri's PhD dissertation N.C. State from 2008 relates similar apparati discussed in the Tong patents that reach the levels of detection of yoctomoles ($10^{-24}$). The named articles, dissertations and patents are incorporated by reference in their entirety. These references give a background into the theories, adjustments and variations upon the technology that are explanatory. Similarly, capillary electrophoresis (CE) has been explained and describe in many patents and journal articles. A current review article gives a good example of the technology as used with peptides "Peptide Separation by Capillary Electrophoresis with Ultraviolet Detection: Some Simple Approaches To Enhance Sensitivity and Resolution," L. Noumie Suragau, *Malaysian Journal of Analytical Sciences*, 15:2 (2011)273-287. This reference gives a current view of CE technology with peptides as an example analyte. Some advantages of CE are: employs capillary tubing within which the electrophoretic separation occurs; adaptable to modern detector technology to give ease of use output; has great efficiencies; requires minute amounts of sample; easily automated for precise quantitative analysis and ease of use; consumes limited quantities of reagents thus making it environmentally friendly; is applicable to a wide selection of analytes.

As used in this specification and in the appended claims, the singular forms "a," an" and "the" include plural references unless the content clearly dictates otherwise.

The use of the word "preferably" in its various forms is explanatory for ease of reading, and should not be used to read into the claims as limiting or anything more.

In describing the invention and embodiments, the following terms will be employed and are intended to be defined as indicated below. If any terms are not fully defined, then the normal usage as used in the art will fill any gaps in the understanding of the terminology.

Laser: is a device that creates a beam of light where all of the photons are in a coherent state—usually with the same frequency and phase. Among the other effects, this means that the light from a laser is often tightly focused and does not diverge much, resulting in the traditional laser beam. In free space, the beams inside and outside the cavity are usually Gaussian distributed and are highly collimated with very small divergence. The distance over which the laser beam remains collimated depends on the square of the beam diameter while divergence angle varies inversely with the beam diameter.

Collimating: is the process of making light rays parallel from a mixture of diverging light rays or beams, and therefore will spread slowly as it propagates. The word is related to "collinear" and implies light that does not disperse with distance (ideally), or that will disperse minimally (in reality). A perfectly collimated beam with no divergence cannot be created due to diffraction, but light can be approximately collimated by a number of processes, for instance by means of a collimator or collimating lens.

Diagnostic flow technology: Is a solid state technology through a series of pumps or pump like mechanisms (such as electroosmotic flow, electrophoretic flow, capillary action, siphoning, pressure, imploding gas bubbles and the like) and apparati move analytes from a sample collection area to an analysis area which comprise of multiple detectors types such as photodiode arrays (PDA), ultraviolet-visible (UV-VIS) spectrometers, charge coupled device (CCD) (such as a CCD-camera) mass spectrometer (MS), Infrared spectrometers (such as Fourier Transform Infrared (FT-IR)}, Nuclear Magnetic Resonance (NMR) detectors, Refractive Index spectrometers (RI), fluorescence detectors, radiation photomultipliers, and the like. Flow can be achieved through liquids, fluids, gas or other means pumped or other means driven through a series of channels and mediums (such as tubing or silica gels) to move analytes from one point to another. Examples would comprise but not limited to Liquid Chromatography (LC) (which would further comprises variations such as micellar, ion exchange and the like), Reverse Phase High Performance Liquid Chromatography (RP-HPLC), Gas Chromatography (GC), High Performance Capillary Electrophoresis (HPCE), Capillary Zone Electrophoresis (CZE), Supercritical Fluid Chromatography (SFC), Sub-critical Fluid Chromatography (SubFC), Inductively Coupled Plasma (ICP), and the like. Each technology is unique unto its own with positives and negatives propagating from each in achieving the needs of the user. For example, capillary electrophoresis has environmental positives in utilizing very little hazardous materials but has negative issues in what substances in what solvents are compatible.

Focal spot: an area or point onto which collimated light parallel to the axis of a lens is focused. This spot of light can be expanded and contracted in different shapes and geometries by some means such as a cylindrical lens.

Absorptive interaction: interaction of analytes in a flow cell chamber or multi channel chamber when the two input beams are mixed and focused in an absorbing medium. These beams form light induced gratings when analytes absorb the excitation light beam. The excited molecules in the form of interference patterns release their heat energy to surrounding solvent or matrix molecules, creating dynamic thermal gratings, and as a result, refractive index gratings. The incoming photons from the probe beam diffract off the gratings to generate the output signal beams.

Multichannel chamber: an enclosed space in which is configured to allow an absorptive interaction between multiple analytes and light beams. Multichannel flow cells and multiple capillary arrays can be situated in a multichannel chamber.

SUMMARY

The embodiments explained and described here utilize techniques to elucidate very small amounts of analyte with high sensitivity, selectivity, resolution and throughput.

The embodiments comprise of a diagnostic flow technology interconnected, configured with or linked to a multiple non linear optical wave mixing technique of a laser source of light absorptively interacting with an analytes either in or passing through the multichannel chamber also known as a laser sensing. Wherein, the interaction of the analyte and beam of light are sensed by photodetectors to a very small molar amount threshold.

The embodiments of the invention can be described by example. In a summary example, a device couples at least two low watt quadruple Nd:YAG laser beams in a unique ultraviolet (UV) wavelength of 266 nm utilizing a non linear wave mixing technique with a capillary electrophoresis diagnostic flow technology utilizing a multi capillary array. This example device can be used to elucidate concurrent multiple non-tagged or non-labeled native proteins that include in their sequence an amino acid picked from at least three amino acid residues of tryptophan, tyrosine, and phenylalanine down to the levels of yoctomoles ($10^{-24}$) and sub-yoctomoles.

Embodiments reaching this yoctomole sensitivity allows for very small injected sample quantities. These levels would have many broad spectrum uses in pharmaceutical, environmental, forensic and anti-terrorism industries. Analyzing such multiple small quantities can increase efficiencies in time and cost in analysis procedures. The embodiments' configurations allow for short optical path lengths which can allow for compact miniaturization of the equipment box. Embodiments of the invention can achieve 100% optical collection efficiencies for signals measured against a dark background.

Implementation of the embodiments comprise methods of analyzing substances through use of a diagnostic flow technology injecting a small amount of analytes into a multichannel chamber, creating simultaneous multiple beams of light through the use of a non linear optical wave mixing technique, eliciting or generating a signal for each analyte, sensing the signal beams, and manipulating and storing the data. Embodiments reaching this yoctomole sensitivity allows for very small injected sample quantities.

An embodiment of the invention utilizes methods of analysis of the combination of technologies. Included in these methods is creating a single or multiple low watt laser beam also known as a light beam or light ray by some laser sensing technology. From simultaneous propagation the laser beams will be guided and manipulated through a series of devices, reflective surfaces such as mirrors, beam traps, beam blockers, beam choppers, beam splitters, focusing lenses, collimating lenses, and concave lenses with an interconnecting to electronic devices including, a computer to both control the front end processes of propagating and manipulating the light source and running the diagnostic flow technology to the back end process of receiving the data and processing it into useable output. Electronics included are photodetectors such as a photodiode detector, an N-type Metal Oxide Semiconductor (NMOS) linked to a photodiode array (PDA) image detector or sensor, to receive the signal light input which could include an amplification of the signal with a photo multiplier tube, a lock in amplifier to filter out extraneous frequencies, a beam chopper controller which controls or segregates the frequency in which the output beam is settled.

As the beam is split with a 70:30 ratio into two beams, the beams are then focused onto a target area of the capillary window in the multi channel chamber where then a cylindrical lens expands the light wave to cover all the capillaries in the capillary arrays. This multi channel chamber is the interaction and interconnection of the diagnostic flow technology with the laser wave mixing. In one embodiment the diagnostic flow technology is an analytical CE device. This device has a source of high voltage with microbore multi capillaries interconnected to an electrophoretic buffer solutions with platinum cathode and an electrophoretic buffer solutions with platinum anode. Other embodiments may have a mass spectrum device connected to the fluidic capillary. The sample interacts with convergent or divergent light beams moving through the target area aperture in the capillary array. After penetrating the capillary array the diffracted signal beams are collimated into a coherent light beam. Other light diffractions and rays are captured in a beam trap. This beam is directed to a beam splitter with the beams sent to photo detector in some embodiments could be photodiode detector and NMOS PDA. The beams are detected and the signal is translated and processed through computer applications to useable data.

BRIEF DESCRIPTION OF DRAWINGS

The objects, advantages, and features of the invention will become more apparent from the following detailed description, when read in conjunction with the accompanying drawing, in which:

FIG. 1. is a schematic of an example embodiment of the invention showing the guided pathway of the dual laser light beams in black and gray for distinction and clarity with the light beam interconnected to a diagnostic flow device capillary electrophoresis.

FIG. 1*a*. is a schematic blow up of the multichannel stage showing a side view of square capillary array. Note that the right side of the figure shows an expansion of the light beam entering the array and the left side shows collinear signal beams leaving the array (does not represent true nature of light beams)

FIG. 1*b*. shows a facial flat planar view of the front of the capillary array window and the capillaries jutting out transverse. Note the shapes used for beams are not necessarily representative of the correct angle of attack on the capillary window.

DETAILED DESCRIPTION

Referring to the embodiments in FIG. 1, a schematic view showing an embodiment of the invention utilizing a capillary array connected to a CE diagnostic flow technology. Two or more laser light sources are contemplated by the embodiments of the invention. Each of the two laser light sources 100*a* and 100*b* emits and presents coherent beams 110*a* and 110*b* to a beam splitter 120 simultaneously. Many sources of laser light are contemplated but lower wattage lasers give advantages to cheaper price and less robust materials in the beam manipulative devices. Preferred laser is the quadrupled Nd:YAG laser emitting 266 nm radiation at a high pulse frequency. Embodiments contemplate different types of lasers. Depending on the techniques used in the cavity, such as Q-switching, mode locking or gainswitching, the laser output may be continuous wave (CW) or pulsed. When the waveform is pulsed, higher peak powers are achieved. Dye lasers and vibronic solid-state lasers can generate a wide range of wavelengths that are appropriate for generating extremely short pulses of light ($10^{-15}$ s). Other types of lasers contemplated are gas such as Argon-ion, chemical, excimer, solid state, photonic crystal, semiconductor, free electron, bio, and exotic. A laser type for implementation of the embodiments contemplated is a solid state Neodynium: yttrium aluminum garnet (Nd:YAG) lasers tuned to 266 nm wavelength suitable for native protein absorption measurements. This UV laser (Model, NU-10210-100, Teem Photonics, France) also offers low power consumption (5 mW) and a good beam quality. Embodiments of the invention can use either higher power (>1 W) or lower power lasers (<1 W). Lower power lasers allow for less damage to optical components, less cost to acquire and to use. To prevent laser damage to optical components and depending on the wavelength ranges and power, there are several optical materials commonly used comprise of borosilicate crown glasses (BK7), UV grade fused Silica, $CaF_2$, $MgF_2$, crystal Quartz, Pyrex and Zerodur.

At beam split, the preferable split ratio of the laser beam is 70:30. Beams 130a and 130b travel to reflective surface or a minor 150 which brings the beam to the beam chopper 170 controlled by chopper controller 180 and lock-in amplifier 190 which among other things amplifies and modulates the cycles of the light wave preferably to 200 Hz. Other cycles are contemplated as the utility demands. The modulated beam 200a and 200b travels to reflective surface or mirror 210 and redirects the beams towards the focusing convex lens 220 preferably 10 cm. The beams are focused onto the capillary window 410 as seen in FIG. 1b of the target area on the capillary array on the multichannel chamber 250. The target areas of each beam on the capillary window can be variable. For example purposes only, beam 200a can be focused on a target area to then be expanded to cover the top four capillaries of an eight capillary array. Similarly beam 200b can be focused on a target area to then be expanded to cover the bottom 4 capillaries of an 8 capillary array. The two separate beams should have minimal overlap on the capillaries after their expansion. After the target areas is focused upon, the beams are expanded by cylindrical lens 230 to cover all the capillary tubes in the array with little overlap. Similarly, the beams 140a and 140b travel to mirror 160 and redirects the beams towards similar focusing and expansion as the preferably lower ratio beam with the focusing convex lens 220 and beam expansion cylindrical lens 230. The beams 140a and 140b should orient before the focusing lens roughly parallel with beams 200a and 200b. The spatial configuration such as distance, size and shape of the lenses allows for the beam focusing and expansion which allows for variable size focal spots and in variable areas on the X, Y, Z coordinate plane of the capillary array window 410 as seen in FIG. 1b similar in function to a flow cell in other applications on the multichannel chamber 250.

Dependent on the materials, type of laser, size of minors and lenses used embodiments of the invention may reach to yoctomoles level in analysis of analytes with for merely an example of analyte of native protein with an amino acid tyrosine in the sequence utilizing a laser at wavelength 266 nm.

Other analytes contemplated but not limited to are cells, biomolecules and small molecules such as labeled or unlabelled tagged and un-tagged proteins, native proteins, peptides, peptidomimetics, polysaccharides, nucleic acids, amino acids, adjuvants, celluloses, biopolymeric molecules, lipids, cell parts, organic compounds, inorganic compounds, antibodies, DNA, RNA, variations on DNA and RNA, nucleotides, drug, drug candidates, biopharmaceuticals, environmental chemicals, astral chemicals, geophysical chemicals, forensic chemicals, chiral, enantiomers, stereoisomers, optical isomers, solids, liquids and gases. At such low levels of concentration the real time analysis or efficient analysis of metabolic chemicals are contemplated.

Contemplated wavelengths of the laser beam are from the below ultraviolet (UV) range through the visible light spectrum beyond the infrared depending on the lasers capabilities and spectral characteristics of the analyte. For example, the UV spectrum for amino acid residue tyrosyl, tryptophanyl, and phenylalanyl reaches a peak of extinction coefficients between 245 nm and 280 nm. Native proteins including L and D versions of the amino acids or residues would be contemplated examples of use of the UV spectrum detection. A laser beam tuned to a unique 266 nm wavelength would be efficient in absorbing an analyte containing these residues. Similarly in another example a protein analyzed with a laser beam tuned to 210 nm or 214 nm would efficiently elucidate the peptide bond whose extinction coefficient reaches its maximum at 190 nm. Other embodiments contemplate UV wavelengths between 10 nm and 400 nm, visible spectrum between 380 and 800 nm and infrared from 740 nm to 300000 nm. Embodiments contemplates individual UV wavelengths or spectrums of wavelengths ranging between 190 nm and 300 nm with other individual UV wavelengths and ranges contemplated such as 210 nm to 280 nm and an individual UV wavelength at 210 nm, 254 nm, 266 nm, and 280 nm.

Now turning to FIG. 1A, the schematic cross-section view shows a blow up of the multichannel chamber 250 held on a rigid translational stage with the view directly into the capillaries 238. The beams 200a and 200b and 140a and 140b are focused then expanded and configured into beams 240a,b,c,d for explanatory purposes of showing that the expanded beams are covering in this case four upper capillaries by black beam 240a and the lower four capillaries by gray beam 240b as the desired target area of the capillary window of the capillary array similar to a sample cell window for demonstration purposes these beams are reflecting the high ratio beams and the unseen 240c and 240d as the low ratio beam. The window should be stabilized and kept vibration free. The photons of the beams interact with the analyte samples flowing through a multichannel capillary window similar to a flow cell, in this embodiment, the multiple signal beams are merely represented by the black beams 245a and the gray beams 245b leave other side of capillary window. The figure shows example beams as collinear but it is not representative of true nature.

The expansion configured beams 240a and 240b is shown in FIG. 1b a front facial planar view of the capillary window 410 the window maybe of variable widths but preferably 0.5 cm of the capillary array 400. The window has an array of eight capillaries 238 with the outer covering removed showing the naked capillary tubing. The four beams are shown entering the capillary window with the upper four capillaries with a transparent black outline expanded to cover all the capillaries in the window representing two beams 240a and 240c and the gray outline representing beams 240b and 240d. These are facial representatives of the beams moving into the capillary to mix together. The angle of the beams entering is not representative.

Analytes are flowed and separated in the capillary array by means of electroosmotic and electrophorectic force by voltage from power supply 220 applying a voltage across anode 220a made from a proper material such as platinum to cathode 220b made from a proper material such as platinum. Any variable amount of capillaries greater than 1 are contemplated for embodiments of the invention. The capillaries may have variable inner diameters (i.d.) and outer diameters (o.d.). The larger net o.d. of each capillary provides larger total capillary surface area per array with larger distance between each capillary probe area. The preferred i.d. is 71 um. The capillaries can be made out of any chemical combination of materials to allow for flow of analyte into the sample staging area and robust enough for any pressures the system would exert on them. The capillaries can be coated (such as polyimide) or uncoated on the outer surface as the experiment demands. The coating should allow for close proximity of the capillaries and allow for light penetration. The capillaries inner wall can be coated (such as polyacrylamide for visible spectrum) or un-coated in the inner surfaces as the experiment demands.

In embodiments utilizing CE, capillaries should be rinsed with water before each run and filled up with a dynamic coating and sieving matrix. An example of a dynamic coating and sieving matrix is a solution comprising 50 mM TRIS borate, 2.5 mM EDTA, 0.5% methylcellulose (high viscosity), 5% Dextran and 0.1% SDS. Solutions should be transparent to applied UV wavelengths.

The capillaries may have different shape geometries for example square or round. The shape can allow among other things good bundling of the capillaries, minimization of background optical noise, less optical scattering and diffraction. The preferred shape is square configured to allow the least amount of gaps minimizing laser leakage between the capillaries. The length of capillary can vary with an effective length being the side that brings the sample analyte to the capillary window for sensing and detection. A preferable effective length is 25 cm. The number of capillaries can also be variable with the needs of the experiment and limitations of the delivery system. The variable amount of the capillaries is greater than 1 such contemplated as 5, 6, 7, 8, 9, 10, 11, 12 and greater than 12. The bundling configuration of the capillaries can be in different 2 dimension or 3 dimension geometries that allow for the best penetration of light, less interference, optical noise, scattering and diffraction. For example, a flat stacked array of capillaries. Means of attaching of the capillaries would be uses of glues, adhesives, or other such attachment means or through the packing configuration of the capillaries in a holder that needs no attaching means. The embodiments have the capability of variable focal point or spot of the beam interacting with the capillaries and can variably be adjusted to track the amount and configuration of the capillaries.

An example to summarize for use in an embodiment utilizing CE and analyzing native unlabeled proteins is the capillaries would be un-coated on the outer surface, fused silica, utilizing a square geometry, an array amount of 10, configured in a stacked configuration creating a flat planar surface and a coating transparent to UV on the inner surface with a 0.5 cm capillary window.

Turning back to FIG. 1, the coherent remnant beams 245a,b,c,d,e,f,g,h after absorptive interaction in passing through the multichannel chamber 250 the beams 245a,b,c,d,e,f,g,h are separated into beams 245c,d,e,f,g,h into beam trap 270 and signal beam 245a and 245b to minor 280 which shifts the beams to a collimating lens 290 which among other things is used to prevent too much signal divergence and to minimize optical interference between capillaries. The beams 295a and 295b are then sent through a beam blocker 298 and into a beam splitter 300 in some ratio preferably 70:30. The beams 305a and 305b are split to a photodiode detector 310 as a control and beams 305c and 305d are split to a multi photospectrometer 320 preferably a NMOS PDA to be detected, stored and analyzed among other data manipulations in the computer 330. It is contemplated analog to digital (A/D) converters would be used as needed by the application. The distance from the capillary window is important in bringing the beams to coherence and parallel without losing intensity.

While the invention has been described in terms of various preferred embodiments and specific examples, the invention should be understood as not being limited by the foregoing detailed description, but as being defined by the appended claims and their equivalents.

What I claim is:

1. A high throughput simultaneously generating ultraviolet multi laser four wave mixing system method comprising of steps:
   a. creating simultaneously at least two low watt UV laser beams,
   b. manipulating the multi laser beams through chopping, splitting, collimating, focusing, and expanding towards a multi array capillary chamber,
   c. charging cathodic and anodic buffer solutions,
   d. sampling multiple minute scale analytes,
   e. electrophorecticly flowing analytes simultaneously into the capillary array apertures,
   f. focusing of the simultaneous beams, said beams correlated to the number of initial laser beams on at least two individual small area targets, said target areas of at least two of capillaries on the capillary array window correlated to each individual beam,
   g. expanding and contracting the simultaneous beams onto the correlated target areas with minimal overlap between said target areas,
   h. collecting a diffracted signal beam and blocking pump and probe beams after penetration into flow cell,
   i. splitting the signal laser beams towards an UV photodiode detector and photodiode array tuned to the UV spectrum,
   j. processing simultaneous signals into useable data.

2. A high throughput apparatus generating ultraviolet laser beams utilizing a four-wave mixing system combined with a multi array capillary electrophoresis and photodetectors functionally integrated further comprising:
   a. computer interconnected to electronic devices,
   b. 266 nm wavelength laser,
   c. second 266 nm wavelength laser,
   a guided pathway for manipulating simultaneous light beams further comprising, a lock in amplifier electronic device, a beam chopper controller electronic device, a beam chopper, a beam splitter set to ratio 70:30, a reflective mirror, a beam blocker, a 10 cm focusing lens, a UV fused silica cylindrical plano-concave lens, a beam trap, a secondary reflective mirror, a collimating lens, a secondary beam blocker, a tertiary reflective mirror, a fourth reflective mirror, a photodiode detector electronic device and a photodiode array detector electronic device,
   e. the electronic device CE further interconnected to the apparatus through a capillary array sample target area further comprising a high voltage source, an electrophoretic buffer, platinum electrodes as a cathode and anode,
   f. microbore fused silica capillary tubing configured to connect the sample to the buffers and to the capillary array chamber,
   g. a multi sample injection port, h. a multi array capillary chamber further comprising of an effective length of 25 cm of 10 square shaped fused silica capillaries with an inner diameter of 71 um stripped of their outer coating 0.5 cm wide glued together in a flat plane creating a capillary window, wherein the improvement comprises of a configuration of simultaneous use of at least two low power laser beams to focus on sets of multiple capillaries simultaneously wherein the apparatus configuration allows high through put analysis with shorter analysis times per sample.

* * * * *